United States Patent [19]

Garner

[11] 4,000,191

[45] Dec. 28, 1976

[54] FLAME RETARDANT PRODUCT OF THE REACTION OF AMMONIA WITH PHOSPHOROUS PENTACHLORIDE-CYANAMIDE INTERMEDIATE

[75] Inventor: Albert Y. Garner, Yellow Springs, Ohio

[73] Assignee: Monsanto Research Corporation, St. Louis, Mo.

[22] Filed: July 22, 1974

[21] Appl. No.: 490,608

[52] U.S. Cl. .................. 260/551 C; 106/15 FP; 252/8.1; 260/551 P; 427/394; 428/276

[51] Int. Cl.$^2$ ............... C07C 125/08; C07F 9/22; C09K 3/28

[58] Field of Search ............... 260/551 P, 551 C

[56] References Cited

UNITED STATES PATENTS

| | | | |
|---|---|---|---|
| 2,782,133 | 2/1957 | Vallette | 106/15 FP X |
| 3,698,854 | 10/1972 | Donaldson et al. | 260/219 X |
| 3,776,950 | 12/1973 | Mitsch | 260/551 P X |
| 3,882,103 | 5/1975 | Beriger et al. | 260/551 P X |

OTHER PUBLICATIONS

"Phosphorous–Nitrogen Compounds", Becke–Goehring et al., CA 72: 100655x (1970).

"Flame–Retardant, Phosphorous-Containing Condensation Products", Nachbur et al., CA 79: 20252t (1973).

"Imparting Flame Retardency to Cotton Knits", Moreau et al., CA 76: 128625u (1972).

*Primary Examiner*—Allen B. Curtis
*Assistant Examiner*—Thomas A. Waltz
*Attorney, Agent, or Firm*—Bruce Stevens

[57] ABSTRACT

Flame retardant protection has been demonstrated on cotton and on polyester-cotton materials by the product obtained from the reaction of cyanamide and PCl$_5$ followed by reaction with anhydrous ammonia in excess of that required to react with the chlorine on the cyanamide and PCl$_5$ intermediate product. Conveniently the material can be treated with an aqueous solution containing a sufficient amount of the new flame retardant compound and the material dried to make the material self extinguishing. Then the treated and dried material is cured at a sufficient temperature to bond the flame retardant to the material. Alternatively and usually preferably, the drying and curing can be accomplished as a single operation.

1 Claim, No Drawings

FLAME RETARDANT PRODUCT OF THE REACTION OF AMMONIA WITH PHOSPHOROUS PENTACHLORIDE-CYANAMIDE INTERMEDIATE

BACKGROUND OF THE INVENTION

1. Field of the invention
Fireproofing.
2. Description of the prior art

One of the older patents in this art is U.S. Pat. No. 2,782,133 teaching aminocyclophosphazene as a fireproofing agent for cellulosic fibers such as cotton. A recent patent is U.S. Pat. No. 3,711,542 teaching certain new N-methylol phosphazene compounds as flame retardants on cotton, and this patent under Background of the Invention contains a summary of certain phosphazene prior art on flameproofing.

SUMMARY OF THE INVENTION

Flame retardant protection has been demonstrated on cotton and on polyester-cotton materials by the product obtained from the reaction of cyanamide and $PCl_5$ followed by reaction with anhydrous ammonia in excess of that required to react with the chlorine on the cyanamide and $PCl_5$ intermediate product. Conveniently the material can be treated with an aqueous solution containing a sufficient amount of the new flame retardant compound and the material dried to make the material self extinguishing. Then the treated and dried material is cured at a sufficient temperature to bond the flame retardant to the material. Alternatively and usually preferably, the drying and curing can be accomplished as a single operation.

DESCRIPTION OF THE PREFERRED EMBODIMENTS

Preparation of product — The structure for the product of the reaction of cyanamide with phosphorus pentachloride, then ammonia is believed to be $$[(NH_2)_3P=N-C\equiv N]_x$$

based on the following reaction

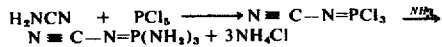

It was hoped that the peraminated compound would be an active monomer analogous to acrylonitrile.

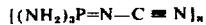

However the infrared spectrum of the crude product does not show nitrile absorption but instead indicates something akin to carbodiimide absorption. This indicates at least a dimeric structure

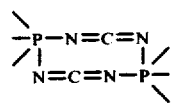

or possibly a linear oligomer. The trichloro-precursor and amminated products are both new compositions.

124½ grams (0.60 m) of $PCl_5$ were added rapidly to a slurry of 25.0 g (0.60 m) of cyanamide (EKC, practical) in 500 ml of chloroform with stirring. There was immediate reaction with the evolution of hydrogen chloride gas. After the initial reaction had subsided, the mixture was heated to reflux and kept there for 18 hours. the resultant, milky slurry was placed under vacuum to remove dissolved hydrogen chloride. An additional 500 ml of chloroform was added followed by the cautious addition of 500 ml of liquid ammonia. The ammonia was contained by a Dry Ice condenser. The excess ammonia was allowed to evaporate overnight.

Evaporation of a sample of the supernatant liquid left no residue. The slurry was mixed with 131.4 g (1.8 m) of diethylamine and refluxed for 7 hours to remove the ammonium chloride as ammonia and chloroform soluble diethylamine.hydrochloride. After standing over the weekend, the white solid was filtered from the red solution and washed with 500 ml of chloroform. The material appeared to be hygroscopic, so it was subjected to vacuum to remove the remaining chloroform, weight 85.0 g.

The infrared spectrum of this product showed —NH absorption and had a moderately strong band at 2155 $cm^{-1}$ which suggests cyclization to give a carbodiimide structure. There was also strong absorption at 6.4 and 8.5$\mu$.

The product, a free-flowing, nonhygroscopic, white powder, was moderately soluble in water yielding a weakly alkaline solution. The material was insoluble in hot cyclohexene, xylene, toluene, THF, DMAC, DMF, pyridine, ethyl acetate, methylene chloride, trichloroethylene, ethanol, nitrobenzene and HMPA. The material shrinks at 93° C in a melting point tube, softens as 120° C forming a soft foam, expanding up the tube. The evolution of gas is noted. The crude product has 19.8% phosphorus and contained chlorine. Recrystallization from water raised the phosphorus content to 22% (theoretical 26%) and the chlorine was almost entirely removed.

| % | Calc'd for $CH_6N_3P$ | Recrystallized Product |
|---|---|---|
| C | 10.10 | 12.10 |
| H | 5.04 | 4.95 |
| N | 58.80 | 48.80 |
| P | 26.10 | 21.89 |
| Cl | 0.00 | 0.30 |

Treatment of fabrics — A solution containing the desired weight percent of the flame retardant reagent in sufficient water to just saturate the cloth was poured on a weighed piece of cloth lying flat in a plastic bag. The solution was worked over the surface of the cloth, until it was uniformly wet. After standing for about fifteen minutes, the cloth was placed in an oven at the desired temperature and dried and cured. After drying and curing, the cloth was allowed to equilibrate before being weighed.

Cure conditions — Cure was effected at 140° C. using the one operation to also dry the wet sample. Formaldehyde and magnesium chloride catalyst were included as an auxiliary treatment in some instances in an attempt to make the material more durable to washing.

Flammability tests — Samples of cloth 10 in. × 3½ in. were clamped in a metal stand and tested according to AATC Test Method 34-1969 using a propane torch in place of the special gas mixture. This flammability test is described in J. Amer. Assoc. Text. Chem. and Colorists 2, (3), 49/19 (1970).

Tabulation of data — The test data are tabulated in the following table. The table is divided into three main sections: Fabric Treatment, Flammability Tests and Miscellaneous Conditions. The following column headings are used. The added notes are for explanation of their meanings where not self explanatory.

| Column | Heading | Explanation |
|---|---|---|
| 1 | Cloth Type | |
| 2 | Reagent | *=Cyanamide/PCl₅/NH₃ product |
| 3 | Auxiliary | material used to bind to cloth such as formaldehyde and catalyst |
| 4 | % Final Add-On | weight percent of product added to the cloth after all processes including laundering if indicated in column 9 |
| 5 | Distance Burned, in. | this represents the length of the sample that was burned out, charred or scorched from the ignited edge |
| 6 | Time, Sec. | time from ignition to removal of flame even though self extinguishment had already occurred |
| 7 | SE (Self Extinguish) | answers question— Did the fire self extinguish before burning the entire sample length? Y=yes; N=no |
| 8 | Cure Temperature | temperature at which the wet cloth was dried and cured |
| 9 | Post Treatment | in a single operation indicates treatment of sample after curing but before flammability test. L=laundered, detergent wash and dried; NL=not laundered |

| Fabric Treatment | | | Flammability Test | | | | Miscellaneous Conditions | |
|---|---|---|---|---|---|---|---|---|
| Cloth Type | Reagent | Auxiliary | % Final Add-On | Distance Burned, in. | Time, Sec | SE | Cure Temp. °C | Post Treatment |
| 65/35 polyester/cotton | * | — | 20.8 | 5 | 30 | Y | 140 | NL |
| 65/35 polyester/cotton | * | — | 12.6 | 10 | | N | 140 | L |
| cotton | * | — | 16.8 | 3½ | 30 | Y | 140 | NL |
| cotton | * | — | 5.78 | 3 | 30 | Y | 140 | L |
| 65/35 polyester/cotton | * | CH₂O, MgCl₂ | 2.8 | 10 | 10 | N | 140 | L |
| cotton | * | CH₂O, MgCl₂ | 3.4 | 10 | 10 | N | 140 | L |
| 65/35 polyester/cotton | * | — | 5.67 | 10 | 15 | N | 140 | L |
| 50/50 polyester/cotton | * | — | 10.8 | 10 | 20 | N | 140 | L |

*Cyanamide/PCl₅/NH₃
SE=Self Extinguishing
Y=Yes
NL=Not Laundered
N=No
L=Laundered
Untreated cotton and cotton/polyester cloths are not self extinguishing in the flammability test.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art of the disclosure. For example, an auxiliary treatment of the cloth with formaldehyde plus a quaternary base or an aminoplast such as trimethylolamine with or without a quaternary base may be useful in making the material more durable to washing with retention of flame retardant properties. Also, other types of cellulose as well as cotton are made flame retardant by the process of the invention, for example, paper and cellulose sponge. Accordingly, modifications are contemplated which can be made without departing from the spirit of the described invention.

What I claim is:

1. A flame-retardant composition comprising the product made by reacting equimolar amounts of cyanamide and PCl₅ followed by reaction with anhydrous ammonia in excess of that required to react with the chlorine on the cyanamide and PCl₅ intermediate product.

* * * * *